(12) United States Patent
Duchamp

(10) Patent No.: US 6,575,934 B2
(45) Date of Patent: Jun. 10, 2003

(54) LOW PROFILE CATHETER

(75) Inventor: Jacky G. Duchamp, Campbell, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/746,416

(22) Filed: Dec. 21, 2000

(65) Prior Publication Data

US 2002/0082549 A1 Jun. 27, 2002

(51) Int. Cl.[7] .............................................. A61M 29/02
(52) U.S. Cl. ................................ 604/102.02; 604/525
(58) Field of Search ....................... 604/102.01, 102.02, 604/102.03, 103.06, 525

(56) References Cited

U.S. PATENT DOCUMENTS

| | | | | |
|---|---|---|---|---|
| 4,921,483 A | | 5/1990 | Wijay et al. ................ 604/96 |
| 4,964,853 A | * | 10/1990 | Sugiyama et al. ...... 604/102.02 |
| 5,370,617 A | * | 12/1994 | Sahota ................ 604/102.02 |
| 5,516,336 A | * | 5/1996 | McInnes et al. ........ 604/102.02 |
| 5,545,149 A | | 8/1996 | Brin et al. .................... 604/265 |
| 5,558,737 A | | 9/1996 | Brown et al. ................ 156/172 |
| 5,700,243 A | * | 12/1997 | Narciso, Jr. ............. 604/102.01 |
| 5,811,043 A | | 9/1998 | Horrigan et al. ............ 264/138 |
| 5,830,181 A | * | 11/1998 | Thornton ............... 604/102.01 |
| 5,951,929 A | | 9/1999 | Wilson ........................ 264/139 |

\* cited by examiner

*Primary Examiner*—Paul J. Hirsch
(74) *Attorney, Agent, or Firm*—Fulwider Patton Lee & Utecht, LLP

(57) ABSTRACT

The invention is directed to an intravascular balloon catheter and a method for forming the same. The catheter includes an elongated shaft having proximal and distal ends, a guidewire receiving lumen extending through at least a distal portion of the elongated shaft; and a balloon on a distal shaft section. A distal portion the guidewire receiving lumen has different stiffness along a length thereof.

14 Claims, 5 Drawing Sheets

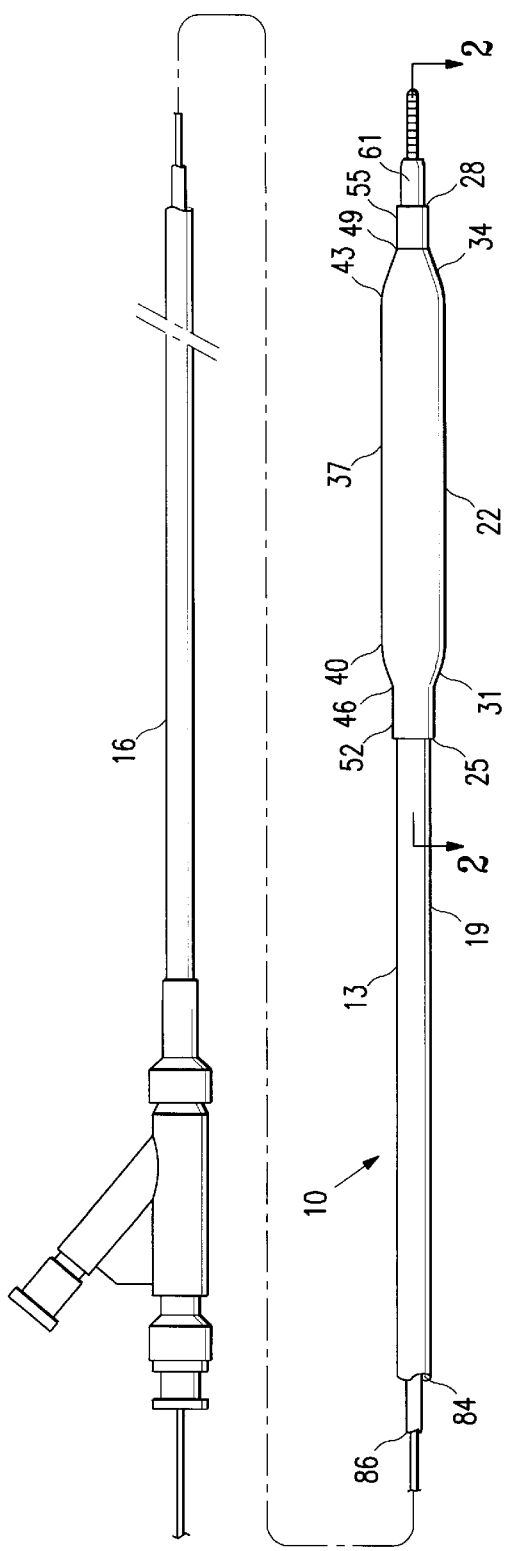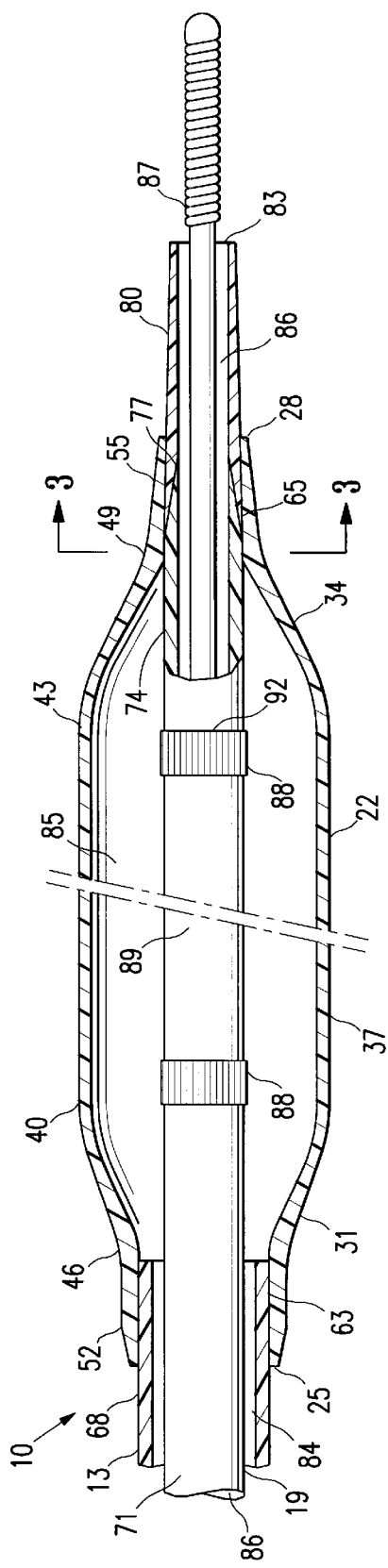

LOW PROFILE CATHETER

FIELD OF INVENTION

The invention relates to the field of intravascular delivery systems, and more particularly to dilatation balloon catheters.

BACKGROUND OF THE INVENTION

In percutaneous transluminal coronary angioplasty (PTCA) procedures, a guiding catheter is advanced until the distal tip of the guiding catheter is seated in the ostium of a desired coronary artery. A guide wire, positioned within an inner lumen of an dilatation catheter, is first advanced out of the distal end of the guiding catheter into the patient's coronary artery until the distal end of the guide wire crosses a lesion to be dilated. Then the dilatation catheter having an inflatable balloon on the distal portion thereof is advanced into the patient's coronary anatomy, over the previously introduced guide wire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the design of catheter balloons, balloon characteristics such as strength, flexibility and compliance must be tailored to provide optimal performance for a particular application. An important consideration in the design of the dilatation catheter assemblies is the flexibility of the distal tip of the catheter at the distal end of the balloon while maintaining the strength of the bond between the catheter and the balloon material. This flexibility affects the ability of the catheter for negotiating through the patient's vasculature without causing injury thereto.

Therefore, what has been needed is a low profile balloon catheter with a flexible distal end while maintaining the integrity of the bond between the catheter and the balloon. The present invention satisfies these and other needs.

SUMMARY OF THE INVENTION

The invention is directed to an intravascular balloon catheter and a method for making the same. The catheter includes an elongated shaft having proximal and distal ends, an inflation lumen extending therein and a guidewire receiving lumen extending through at least a distal portion of the elongated shaft, and an inflatable balloon disposed on a distal shaft section. The distal shaft section of the catheter has a distal end, a port in the distal end. At least a part of the guidewire receiving lumen extends within the distal shaft section to the port in the distal end. At least part of the inflation lumen extends within the distal shaft section to a location proximal to the distal end of the distal shaft section. A distal portion of the guidewire receiving lumen has different hardness along a length thereof. In one embodiment, the distal portion of the guidewire receiving lumen is formed from two different sections. In an embodiment, the distal section of the two sections is softer than the proximal section. The two sections can be formed of similar material with different stiffness values or alternatively of different materials.

In one embodiment, the balloon has proximal and distal ends, proximal and distal tapered regions and an intermediate region longitudinally disposed therebetween. The proximal and distal regions each has a first end adjacent the intermediate region and a second end opposite the first end. A balloon distal shaft is disposed between the balloon distal tapered region second end and the balloon distal end. At least a portion of the balloon distal shaft sealingly extends over at least a portion of the two different sections forming the distal portion of the guidewire lumen and forms a distal shaft overlap. In one embodiment, the distal shaft overlap has a longitudinal dimension greater than the longitudinal dimension of the balloon distal tapered region, as measured along a catheter longitudinal axis.

In a method for making an intravascular balloon catheter, an elongated shaft is provided having proximal and distal ends, an inflation lumen extending therein and a guidewire receiving lumen extending through at least a distal portion of the elongated shaft to a shaft distal end; and an inflatable balloon on a distal shaft section of the elongated shaft as described above. A tubular member is provided having proximal and distal ends and formed of a material softer than a material forming the distal portion of the catheter shaft guidewire receiving lumen. The soft tubular member has at least one longitudinal incision along the tubular member extending from the tubular member proximal end to a point proximal to the tubular member proximal end. The proximal end of the tubular member is extended over the distal end of the catheter distal shaft section forming a distal shaft overlap, with a distance between two surfaces on two sides of the at least one incision increasing in the proximal direction to form a wedge. A mandrel is inserted into the catheter shaft guidewire receiving lumen and extends distally to a point proximal to the tubular member proximal end. The balloon distal shaft is radially disposed over the distal shaft overlap. A protective sleeve is disposed over the distal shaft overlap and energy to produce sufficient heat to melt the materials in the distal shaft overlap is directed onto the distal shaft overlap area to effect a seal in the distal shaft overlap area. The protective sleeve is thereafter removed.

The seal of the overlap area may be first formed between the proximal portion of the tubular member and the distal portion of the shaft guidewire lumen before the balloon distal shaft is disposed over that area with the seal between the balloon distal shaft and the overlap area being formed in a subsequent sealing step. In the alternative, the seal may be accomplished in a single sealing step between the proximal portion of the tubular member, the distal portion of the shaft guidewire lumen, and the balloon distal shaft.

BRIEF DESCRIPTION OF THE DRAWINGS

FIG. 1 is an elevational view of a balloon catheter embodying features of the invention.

FIG. 2 is a longitudinal cross-sectional view of the catheter shown in FIG. 1 taken along lines 2—2.

DETAILED DESCRIPTION OF THE INVENTION

Figure 3:
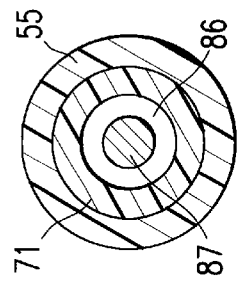
FIG. 3 is a cross sectional view of the balloon catheter of FIG. 1 taken along lines 3—3.

In the embodiment features of which are illustrated in FIG. 1, the catheter 10 of the present invention is a balloon catheter having an elongated catheter shaft 13 having a proximal section 16 and a distal section 19 with an inflatable balloon 22 on the distal section 19 of the shaft 13 and in surrounding relationship thereto. The balloon 22 has proximal and distal ends 25 and 28, proximal and distal tapered regions 31 and 34, and an intermediate region 37 longitudinally disposed between the proximal and distal tapered regions 31 and 34. The proximal and distal tapered regions 31 and 34 each has a first end 40 and 43, respectively, adjacent the intermediate region 37, and a second end 46 and 49 opposite their respective first ends, 40 and 43. A balloon proximal shaft 52 extends between the balloon proximal taper second end 46 and the balloon proximal end 25 and a distal shaft 55 extends between the balloon distal taper second end 49 and the balloon distal end 28. A stent (not shown) may be mounted on at least a portion of the intermediate region 37 to form a stent delivery catheter system.

In the embodiment features of which are illustrated in FIGS. 1 through 4, the catheter shaft 13 comprises an outer tubular member 68, an inner tubular member 71 having a distal portion 74 with a distal end 77, and a soft distal tip 80 having a distal end 83; the inner tubular member 71 defining, with the outer tubular member 68, an inflation lumen 84, in fluid communication with a balloon interior chamber 85. The inner tubular member 71 has an inner lumen 86 extending therein configured to slidably receive a guidewire 87 suitable for advancement through a patient's coronary arteries. The balloon 22 is bonded, preferably fusion bonded, to the outer tubular member 68 by the proximal fusion bond 63, and to the inner tubular member 71 and the distal soft tip 80 by the distal fusion bond 65. The one or more bonds are each formed at an interface between the shaft 13 and the balloon 22. The longitudinal dimension of the bonds, as shown in some the figures, is for illustrative purposes only and is not necessarily meant as an exact graphical representation of the bonds' proportional length, unless otherwise stated.

Preferably, at least one marker 88, is located on a portion 89 of the inner member 71 extending within the interior 85 of the balloon 82. In a preferred embodiment, a distal edge 92 of the marker 88 is radially lined up with the first end 43 of the balloon distal taper 34.

Figure 4:
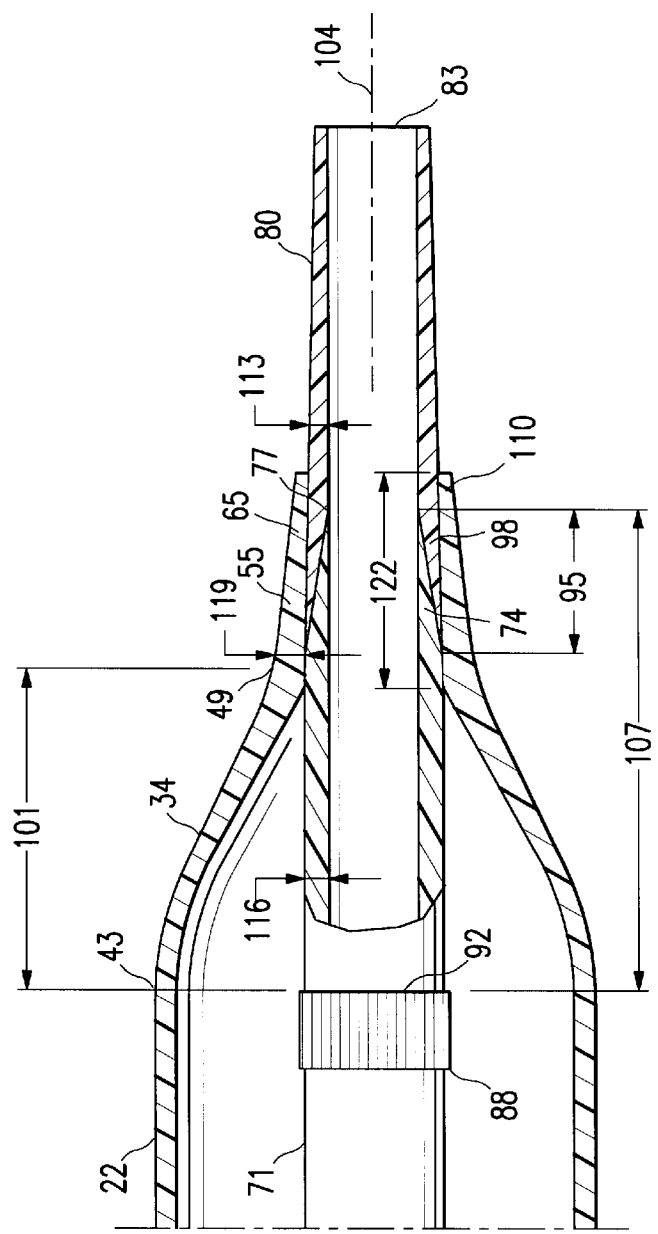
FIG. 4, is an enlarged longitudinal cross-sectional, partially cut away, view of the balloon catheter of FIG. 1, showing the sealed area between the balloon distal shaft, the distal inner member, and the distal tip.

As best can bee seen in FIG. 4, an overlap portion 95 is formed between a proximal portion 98 of the soft distal tip 80, the distal portion 74 of the inner tubular member 71, and the distal balloon shaft 55. In a presently preferred embodiment, the longitudinal dimension of the overlap 95 portion ranges from about 0.25 to about 1.00 millimeter (mm), preferably, from about 0.25 to about 0.50 mm.

Preferably, a tapered longitudinal dimension 101 between the balloon distal taper first end 43 and the balloon distal taper second end 49, as measured along a catheter shaft longitudinal axis 104, ranges from about 2.5 to about 3.5 mm, preferably, from about 2.5 to about 3.0 mm (based on a 3.0 mm balloon).

Preferably, a longitudinal dimension 107 of the inner member 71, as measured from the distal edge 92 of the marker 88 to the distal end 77 of the inner member 71, is longer than the tapered longitudinal dimension 101 by at least about 1 mm, preferably, by at least about 0.25 mm.

In a presently preferred embodiment, the distal balloon shaft 55 has a longitudinal dimension ranging from about 1 to about 2.5 mm, preferably from about 1 to about 1.5 mm. Preferably, the distal balloon shaft 55 has an extended portion 110 extending distally beyond the distal end 77 of the inner member 71, the distally extending portion 110 ranging from about 0.25 to about 2 mm, preferably, from about 0.25 to about 1 mm.

Preferably, the soft distal tip 80 at its distal end 83 has an outer diameter (OD) smaller than its OD at its proximal portion 98. Preferably, before assembly, the OD of the soft distal tip 80 at its proximal portion 98 is smaller than the OD of the inner member 70 at its distal portion 74. Similarly, a wall thickness 113 of the soft distal tip 80 is smaller than a wall thickness 116 of the inner member 71 at its distal portion 74. In a presently preferred embodiment, the OD of the soft distal tip 80 at its proximal portion 98 ranges from about 0.018 to 0.025 inch, preferably, from about 0.019 to about 0.022 inch, and tapers to an OD at the soft distal tip distal end 83, ranging from about 0.016 to about 0.019 inch, preferably, from about 0.016 to about 0.017 inch. Preferably, the wall thickness 113 of the soft distal tip 80 ranges from about 0.002 to about 0.005 inch, preferably, from about 0.002 to about 0.003 inch. Preferably, the inner member 71 at its distal portion 74, has an OD ranging from about 0.0195 to 0.0235 inch, preferably, from about 0.0205 to about 0.0215 inch; and the wall thickness 116 ranging from about 0.002 to about 0.006 inch, preferably, from about 0.003 to about 0.004 inch.

In a presently preferred embodiment, a wall thickness 119 of the balloon distal shaft 55 may be reduced prior to the formation of the distal seal 65, using methods such as sanding.

The longitudinal dimension of the proximal and distal bonds 63 and 65, independently, may range from about 0.25 to about 1.5 millimeters (mm), preferably, from about 0.25 to about 1 mm. In one embodiment, the distal fusion bond 65 has a longitudinal dimension extending along at least a portion of the distal tapered region 34 of the balloon 22 toward the intermediate region 37, ranging from about 0.05 to about 1 mm; preferably from about 0.2 to about 0.3 mm.

The soft distal tip 80 has a stiffness lower than that for the distal portion 74 of the inner member 71.

The distal tip member 80 is preferably softer than the inner member 71 or at least the distal portion 74 thereof, to provide improved catheter maneuverability and decrease the risk of damage to the patient's vessel during advancement of the catheter therein. The tip member is typically formed of a polymeric material having a Shore Durometer hardness which is lower than the Shore Durometer hardness of the polymeric material forming at least the distal portion of the inner member. Preferably, the inner member 71, or at least the distal portion 74 thereof, has a stiffness ranging from about 63 to about 80, preferably, from about 63 to about 72 durometers; while the soft distal tip 80 has a stiffness ranging from about 55 to about 70, preferably, from about 55 to about 63 durometers.

The Shore Durometer hardness of the polymeric material forming the tip member is about 35 D to about 63 D, preferably about 40 D to about 55 D. In a presently preferred embodiment, the tip member and the inner member (or at least in the distal portion thereof) are independently, at least in part, formed of a polyether block amide polymers such as those available from Atochem under the trade name PEBAX; polyesters available from Dutch State Mines under the trade name ARNITEL; block copolymers such as those sold under the trade name TECOPLAST and available from Thermedics; polyester block copolymers (containing one or more of the following glycols) comprising hard segments of polyethylene-terephthalate or polybutylene-terephthalate, and soft segments of polyether such as polyethylene glycol, polypropylene glycol or polytetramethylene glycol ethers, such as those available under the tradename HYTREL available from DuPont; polyolefin based copolymers such as a polyethylene based adhesive polymers such as an ethylene-acrylic acid copolymer which is sold commercially as PRIMACOR by Dow Chemical Co.; high density polyethylene (HDPE); polyurethanes including polyurethane block copolymers such as PELLETHANE (a polyester based polyurethane, available from Dow Plastics); nylons; or any blends thereof.

The preferred materials for forming the soft distal tip 80 and the inner member 71 (or at least the distal portion 74 thereof), independently include, polyether block amide polymers such as PEBAX (such as 70 D, 63 D, 55 D, 40D); polyurethane block copolymers include polyester based polyurethanes such as PELLETHANE (such as 75 D);or blends thereof.

Suitable material for forming the balloon 22 include: PEBAX (including 70 D and other blends); PELLATHANE (including 75d); nylones (including Nylon 11, 12); HYTREL; ARNITEL; or blends thereof.

FIGS. 5(A) through 5(I), wherein like reference indicate like features, illustrate features of a presently preferred method for making the catheters of the present invention.

Figure 5A:
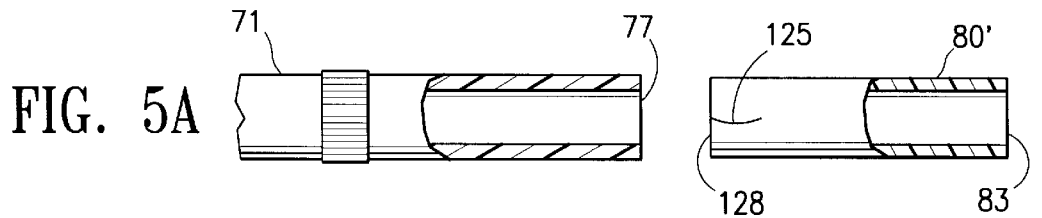
FIGS. 5(A) through 5(I) show a preferred process for forming catheters embodying features of the present invention.
Figure 5B:
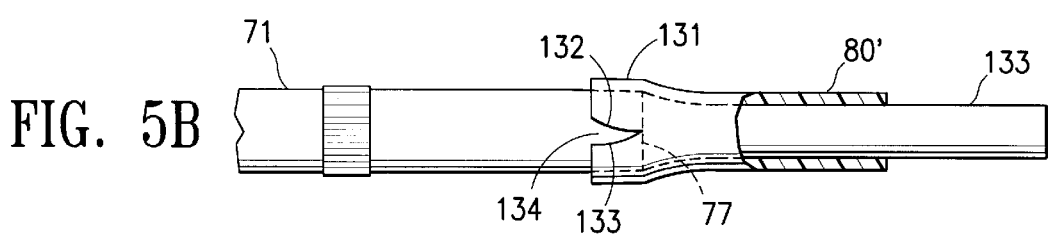
Figure 5C:
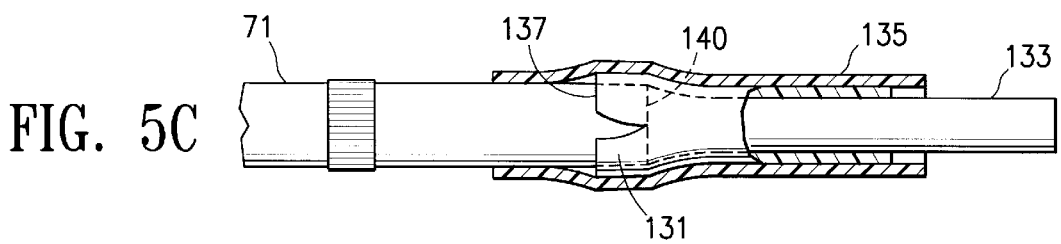
Figure 5D:
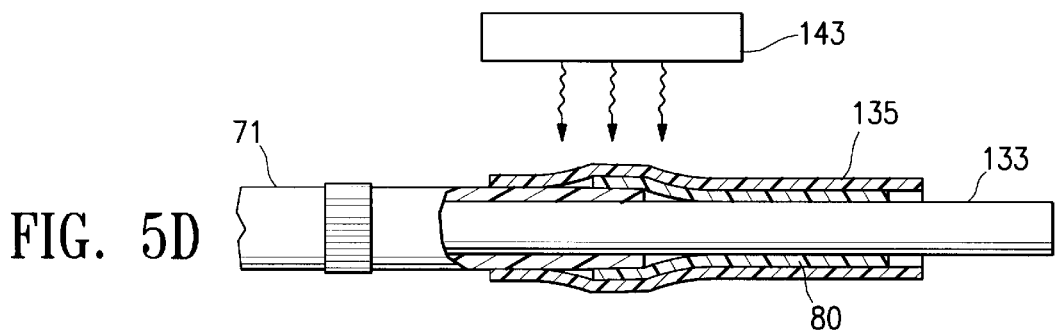
Figure 5E:
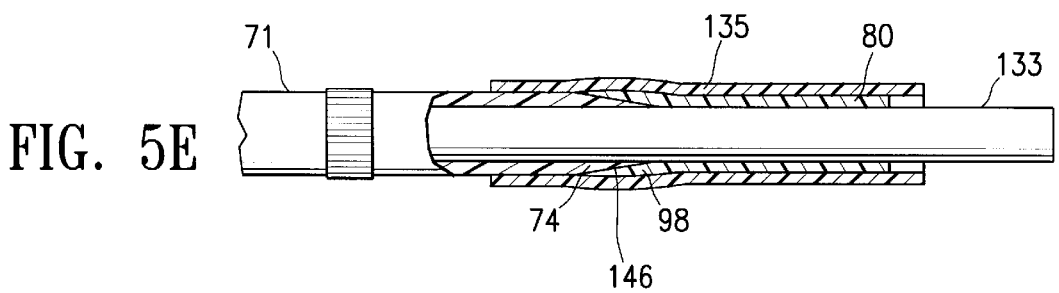
Figure 5F:
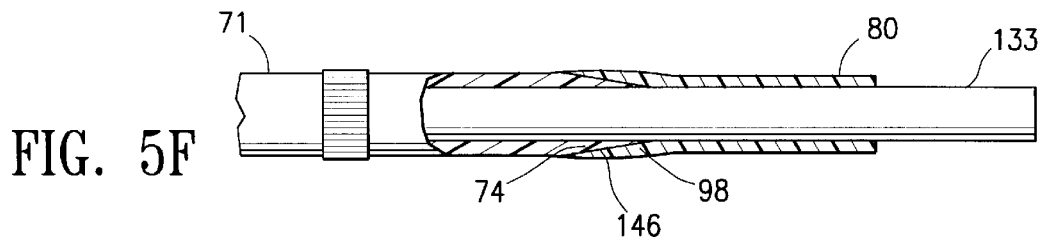
Figure 5G:
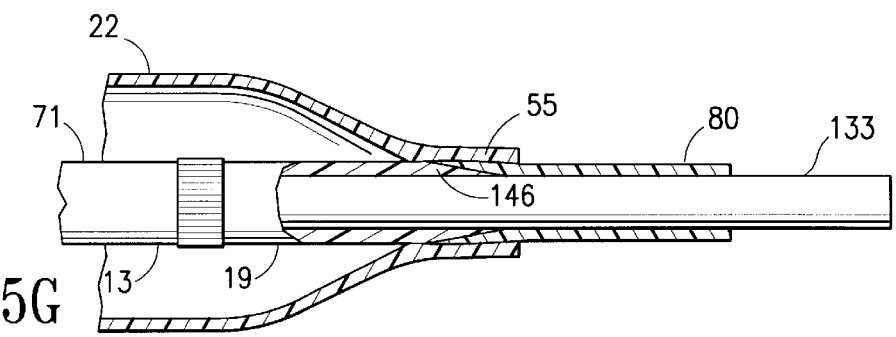
Figure 5H:
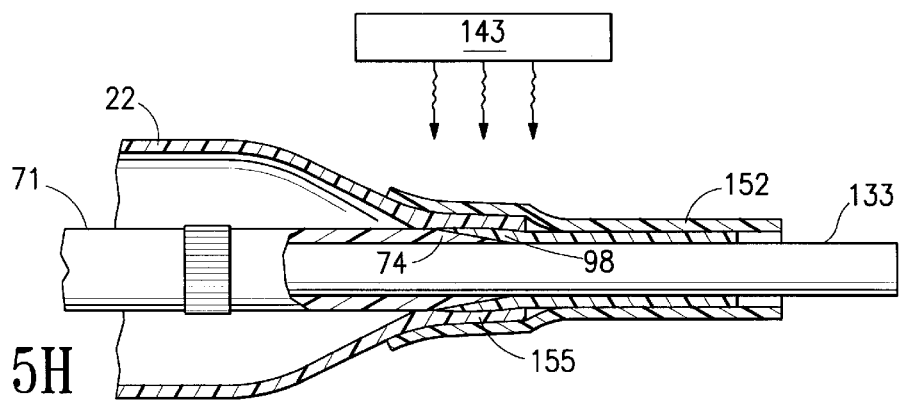
Figure 5I:
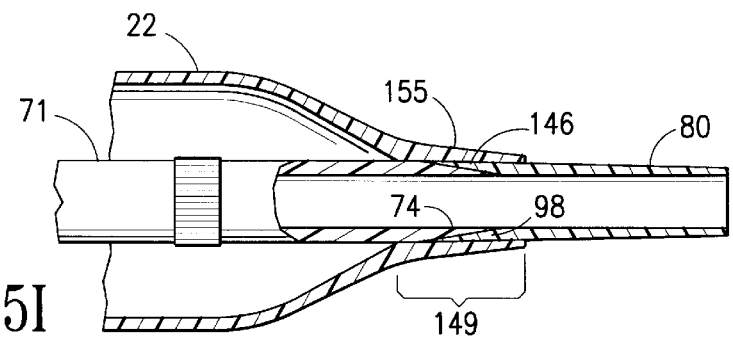

As illustrated in FIG. 5A, a soft tubular member 80' (for forming the soft distal tip 80) is provided along with the inner tubular member 71, a distal portion 74, of which is being shown. One or more longitudinal incisions 125 are made, using suitable means such as a sharp object or laser, along the tubular member 80' in the longitudinal direction, from a soft tubular member 80' proximal end 128 to a point proximal to the soft tubular member distal end 83. The incision 125 has a longitudinal dimension ranging from about 0.1 to about 0.5 mm, preferably, from about 0.1 to about 0.25 mm.

The proximal end 128 of the soft tubular member 80' and the distal end 77 of the inner member 71 are brought together, with the soft tubular member proximal end 128 overlapping the inner member distal end 77, forming an overlap 131, with the distance between two surfaces on the two sides 132 and 133 of the incision 125 increasing in the proximal direction to form a wedge 134. A mandrel 133 is inserted into the inner tubular member 71 extending proximally from the inner tubular member distal end 77 to a point proximal to the soft tubular member proximal end 128.

A shrink tubing 135 is placed over the overlap 131, the tubing 135X, preferably, extending beyond proximal 137 and distal 140 ends of the overlap 131.

A Substantially monochromatic energy from a heat source 143, at a wavelength of maximum spectral absorption of the materials forming the inner member distal portion 74 and the soft tubular member 80', is controllably applied to the overlap area 131 producing sufficient heat to melt the materials forming the overlap 131.

The melted area is then cooled forming a distal elongated member seal 146 between the inner member distal portion 74 and the proximal portion 98 of the soft distal tip 80.

The shrink tubing 135 is then removed, leaving the joined inner member 71 and the soft tip 80.

The balloon 22 is then radially disposed over the distal section 19 of the shaft 13, such that the balloon distal shaft 55 forms a balloon distal overlap 149 over the distal elongated member seal 146, previously formed between the inner member 71 and the soft distal tip 80.

A shrink tubing 152 is placed over the balloon distal overlap 149 and the materials are melted again using the laser source laser source 143 (or other suitable sources), with the shrink tubing 152 and the mandrel 133 thereafter removed, forming the catheter of the present invention.

Figure 6A:
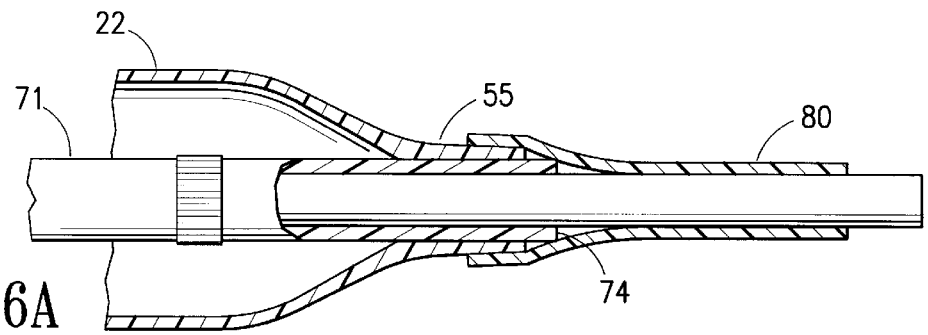
FIGS. 6(A) through 6(D) show alternate processes for forming catheters embodying features of the present invention.
Figure 6B:
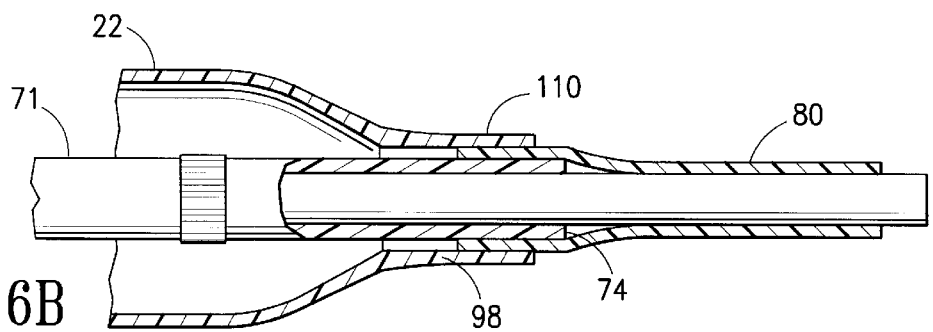

Alternatively, as illustrated in FIG. 6A, the balloon distal shaft 55 may be first sealed to the inner member 71, with the soft tip 80 being extended over at least a portion of the balloon distal shaft 55 and the inner member distal portion 74, subsequently. Alternatively, as shown in FIG. 6B, the soft tip 80 may be extended over the inner member distal portion 74, with the balloon distal shaft extended portion 110 overlaying the soft tip proximal portion 98.

Figure 6C:
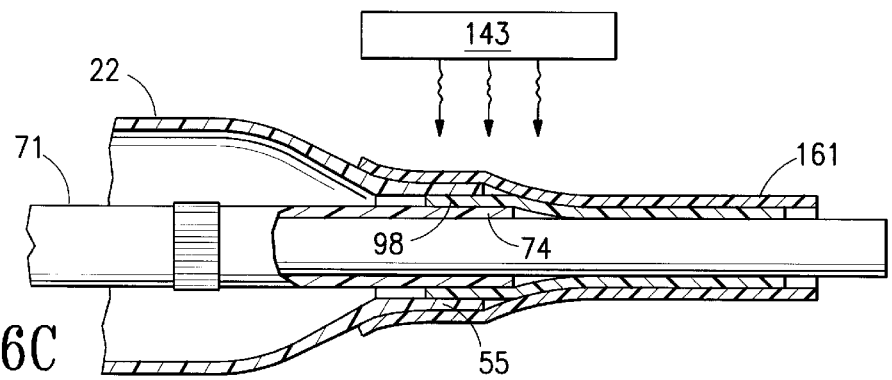
Figure 6D:
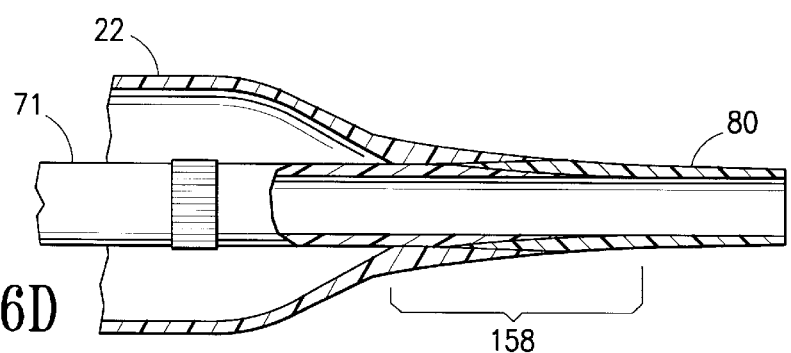

In yet another alternate method and shown in FIGS. 6C–6D, the soft tip proximal portion 98, the inner member distal portion 74, and at least a portion of the balloon distal shaft 55, form a combined distal overlap 158. A tubular shrink tubing 161 is then placed over the combined distal overlap 158, with subsequent melting of the material forming the overlap 158. In this embodiment, in forming the overlap 158 prior to the melting step, the balloon distal shaft 55 may be the outer most layer, or may be placed between the inner member distal portion 74 and the soft tip proximal portion 98.

The shrink tubings 135, 152, and 161 may all be formed of similar material, suitable material for forming the shrink tubings include, LDPE, UDPE, preferably, LDPE, UDPE.

The presently preferred fusion heat source, 143, is a $CO_2$ laser. The laser power is about 50 mW to about 250 mW, the laser rotation speed about the members to be bonded is about 75 to about 300, and the laser absolute focus is about 0.30 to about 0.50. The materials are heated at temperatures between about 100° C. to about 200° C. for about 30 to about 150 seconds.

While particular forms of the invention have been illustrated and described, it will be apparent that various modifications can be made without departing from the spirit and scope of the invention. Accordingly, it is not intended that the invention be limited, except as by the appended

What is claimed is:

1. An intravascular balloon catheter, comprising:
   an elongated shaft having proximal and distal ends, an inflation lumen extending therein and a guidewire receiving lumen extending through at least a portion of the elongated shaft;
   a distal shaft section having a distal end, a port in the distal end, at least part of the guidewire receiving lumen extending within the distal shaft section to the port in the distal end, and at least a part of the inflation lumen extending within the distal shaft section to a location proximal to the distal end of the distal shaft section, a distal portion of the guidewire receiving lumen being defined by a hard portion and a soft portion of said elongated shaft, wherein said soft and hard portions are joined in an overlapping region; and an inflatable balloon on the distal shaft section having an interior in fluid communication with the inflation lumen therein and having proximal and distal ends, proximal and distal tapered regions and an intermediate region longitudinally disposed therebetween, the proximal and distal regions each having a first end adjacent the intermediate region and a second end opposite the first end, and a balloon distal shaft disposed between the balloon distal tapered region second end and a balloon distal end, shaft, wherein said distal shaft extends about said overlapping region and to a point distal thereto to form a distal shaft overlap.

2. The catheter of claim 1 wherein the distal portion of the guidewire receiving lumen is tapered in the distal direction.

3. The catheter of claim 1 wherein the hard portion and soft portion are formed from two different materials.

4. The catheter of claim 1 wherein the distal shaft overlap has a longitudinal dimension ranging from about 0.25 to about 1.0 millimeters.

5. The catheter of claim 4 wherein the distal shaft overlap has a longitudinal dimension ranging from about 0.25 to about 0.5 millimeters.

6. The catheter of claim 1 wherein the balloon distal tapered region has a longitudinal dimension, as measured along a catheter longitudinal axis, ranging from about 2.5 to about 3.5 millimeters.

7. The catheter of claim 6 wherein the balloon distal tapered region has a longitudinal dimension, as measured along a catheter longitudinal axis, ranging from about 2.5 to about 3 millimeters.

8. The catheter of claim 1 wherein the distal shaft overlap has a longitudinal dimension greater than the longitudinal dimension of the balloon distal tapered region, as measured along a catheter longitudinal axis.

9. The catheter of claim 8 wherein the distal shaft overlap longitudinal dimension is greater than the longitudinal dimension of the balloon distal tapered region by at least about 1 millimeter.

10. The catheter of claim 9 wherein the distal shaft overlap longitudinal dimension is greater than the longitudinal dimension of the balloon distal tapered region by at least about 0.25 millimeter.

11. The catheter of claim 1 wherein the hard portion and soft portion are formed of similar material.

12. The catheter of claim 11 wherein the soft portion is distal to the hard portion.

13. The catheter of claim 3 wherein the soft portion is distal to the hard portion.

14. The catheter of claim 1 wherein said distal shaft extends to a point proximal to said overlapping region to form said distal shaft overlap.

* * * * *